US005559123A

United States Patent [19]
Somers et al.

[11] Patent Number: 5,559,123
[45] Date of Patent: Sep. 24, 1996

[54] DERIVATIVES OF BENZOYLECGONINE, ECGONINE AND ECGONIDINE AND METHODS FOR PREPARING AND USING SAME

[75] Inventors: Lowell M. Somers, Indio, Calif.;
James E. Wynn, Summerville, S.C.

[73] Assignee: Entropin, Inc., Indio, Calif.

[21] Appl. No.: 320,050

[22] Filed: Oct. 7, 1994

Related U.S. Application Data

[62] Division of Ser. No. 999,307, Dec. 31, 1992, Pat. No. 5,376,667.

[51] Int. Cl.$^6$ .................... A61K 31/46; C07D 451/02; C07D 451/04
[52] U.S. Cl. .................. 514/304; 546/127; 546/130; 546/131
[58] Field of Search ............................ 514/304; 546/127, 546/130, 131

[56] References Cited

U.S. PATENT DOCUMENTS

| | | | |
|---|---|---|---|
| 2,893,996 | 7/1959 | Rudner et al. | 260/292 |
| 2,948,730 | 8/1960 | Rudner et al. | 260/292 |
| 4,469,700 | 9/1984 | Somers | 424/265 |
| 4,512,996 | 4/1985 | Somers | 514/304 |
| 4,556,663 | 12/1985 | Somers | 514/304 |

OTHER PUBLICATIONS

W. H. Anderson and D. T. Stafford, "Applications of Capillary Gas Chromatography in Routine Toxicological Analyses", *High Resolut. Chromatogr., Chromatogr. Commun.*, 6(5), pp. 247–254 (1983).
M. R. Bell and S. Archer, "L(–)-2-Tropinone", *J. Amer. Chem. Soc.*, 82, pp. 4642–4644 (1960).
R. Bingham, "Esterene in the Treatment of Rheumatoid Arthritis", *Arthritis News Today*, 2(7), pp. 1–4 (1980).
C. S. Boyer and D. R. Peterson, "Enymatic Basis for the Transesterification of Cocaine in the Presence of Ethanol: Evidence for the Participation of Microsomal Carboxylesterase", *J. Pharmacol. Exp. Ther.*, 260(3), pp. 939–946 (1992).
M. R. Brzezinski et al., "Convenient Synthesis of Benzoylecgonine Ethyl Ester, a Homolog of Cocaine", *Synth. Commun.*, 22(7), pp. 1027–1032 (1992).
R. D. Budd., "Cocaine Radioimmunoassay—Structure Versus Reactivity", *Clin. Toxicol.*, 18(7), pp. 773–782 (1981).
D. T. Chia and J. A. Gere, "Rapid Drug Screening Using Toxi–Lab Extraction Followed by Capillary Gas Chromatography/Mass Spectroscopy", *Clin. Biochem.*, 20(5), pp. 303–306 (1987).
E. J. Cone et al., "Testing Human Hair for Drug Abuse. II. Identification of Unique Cocaine Metabolites in Hair of Drug Abusers and Evaluation of Decontamination Procedures", *J. Anal. Toxicol.*, 15(5), pp. 250–255 (1991).
R. A. Dean et al., "Human Liver Cocaine Esterases: Ethanol–Mediated Formation of Ethylcocaine", *FASEB J.*, 5(12), pp. 2735–2739 (1991).

J. R. Fozard et al., "Structure–Activity Relationship of Compounds Which Block Receptors for 5–Hydroxytryptamine on the Sympathetic Nerves of the Rabbit Heart", *Br. J. Pharmacol.*, 61(3), pp. 499P–500P (1977).
F. Fish and W. D. C. Wilson, "Excretion of Cocaine and its Metabolites in Man", *J. Pharm. Pharmac.*, 21 suppl., pp. 135s–138s (1969).
J. R. Fozard et al., "Structure–Activity Relationship of Compounds Which Block Receptors for 5–Hydroxytryptamine on the Sympathetic Nerves of the Rabbit Heart", *Br. J. Pharmacol.*, 61(3), pp. 499P–500P (1977).
J. R. Fozard et al., "Blockade of Serotonin Receptors on Autonomic Neurones by (–)-Cocaine and Some Related Compounds", *Eur. J. Pharmacol.*, 59(3–4), pp. 195–210 (1979).
J. M. G. Galvez and A. P. de Abram, "Cocaina: Avances en su Investigation", *Bol. Soc. Quim. Peru*, 56(1), pp. 12–20 (Galvez) 1989.
W. L. Hearn et al., "Cocaethylene is More Potent than Cocaine in Mediating Lethality", *Pharmacol., Biochem. Behav.*, 39(2), pp. 531–533 (1991).
W. L. Hearn et al., "Cocaethylene: A Unique Cocaine Metabolite Displays High Affinity for the Dopamine Transporter", *J. Neurochem.*, 56(2), pp. 698–701 (1991).
G. W. Hime et al., "Analysis of Cocaine and Cocaethylene in Blood and Tissue by GC–NPD and GC–ion Trap Mass Spectrometry", *J. Anal. Toxicol.*, 15(5), pp. 241–245 (1991).
P. Jatlow et al., "Cocaethylene: A Neuropharmacologically Active Metabolite Associated with Concurrent Cocaine–Ethanol Ingestion", *Life Sci.*, 48(18), pp. 1787–1794 (1991).
J. L. Katz et al., "Comparative Behavioral Pharmacology and Toxicology of Cocaine and its Ethanol–Derived Metabolite, Cocaine Ethyl–Ester (Cocaethylene)", *Life Sci.*, 50(18), pp. 1351–1361 (1992).
A. H. Lewin, "2β–Substituted Analogs of Cocaine. Synthesis and Inhibition of Binding to the Cocaine Receptor", *J. Med. Chem.*, 35(1), pp. 135–140 (1992).
T. Lukaszewski and W. K. Jeffery, "Impurities and Artifacts of Illicit Cocaine", *J. Forensic Sci.*, 25(3), pp. 499–507 (1980).
H. H. McCurdy, "Quantitation of Cocaine and Benzoylecgonine after JETUBE Extraction and Derivitazation", *J. Anal. Toxicol.*, 4(2), pp. 82–85 (1980).

(List continued on next page.)

*Primary Examiner*—C. Warren Ivy
*Assistant Examiner*—Evelyn Huang
*Attorney, Agent, or Firm*—Fish & Neave; Denise L. Loring; Jeffrey D. Hsi

[57] ABSTRACT

The present invention relates to a novel class of benzoylecgonine, ecgonine and ecgonidine derivatives which are useful for preventing and treating immunoregulatory disorders, neuromuscular disorders, joint disorders, connective tissue disorders, circulatory disorders and pain. The compounds of this invention are conveniently obtained by chemical synthesis. Accordingly, this invention also relates to methods for preparing the benzoylecgonine, ecgonine and ecgonidine derivatives and to pharmaceutical compositions containing these derivatives.

15 Claims, No Drawings

*Medical World News*, "FP Giving Cocaine for Arthritis is Beset But Gains a Major Ally", pp. 19–20 (1979).

A. L. Misra et al., "Physiologic Distribution and Metabolism of [³H]–Benzoylecgonine (Cocaine Metabolite) in the Rat", *Res. Commun. Chem. Pathol. Pharmacol.*, 8, pp. 55–63 (1974).

A. L. Misra and S. J. Mule, "Calcium–Binding Property of Cocaine and Some of its Active Metabolites—Formation of Molecular Complexes", *Res. Comm. Chem. Pathol. Pharmacol.*, 11(4), pp. 663–669 (1975).

A. L. Misra et al., "Disposition of [³H]–Benzoylecgonine (Cocaine Metabolite) in the Rat", *Res. Commun. Chem. Pathol. Pharmacol., 13(4), pp. 579–584 (1976)*.

A. L. Misra et al., "Estimation and Disposition of [³H]–Benzoylecgonine and Pharmacological Activity of Some Cocaine Metabolites", *J. Pharm. Pharmac.*, 27, pp. 784–786 (1975).

C. Moore et al., "Determination of Cocaine and its Metabolites in Brain Tissue Using High–Flow Solid–Phase Extraction Columns and High–Performance Liquid Chromatography", *Forensic Sci. Int.*, 53(2), 215–219 (1992).

S. Mule et al., "Intracellular Disposition of [³H]–Cocaine, [³H]–Norcocaine, [³H]–Benzoylecgonine and [³H]–Benzoylnorecgonine in the Brain of Rats", *Life Sci.*, 19, pp. 1585–1596 (1976).

M. Perez–Reyes and A. R. Jeffcoat, "Ethanol/Cocaine Interaction: Cocaine and Cocaethylene Plasma Concentrations and Their Relationship to Subjective and Cardiovascular Effects", *Life Sci.*, 51(8), pp. 553–563 (1992).

M. Polasek et al., "Determination of Limiting Ionic Mobilities and Dissociation Constants of Some Local Anaesthetics", *J. Chomatogr.*, 596, pp. 265–270 (1992).

F. K. Rafla and R. L. Epstein, "Identification of Cocaine and its Metabolites in Human Urine in the Presence of Ethyl Alchohol", *J. Anal. Toxicol.*, 3(2), pp. 59–63 (1979) R33 (5/5), R39(20/20).

M. E. A. Reith et al., "Locomotor Effects of Cocaine, Cocaine Congeners and Local Anesthetics in Mice", *Pharmacol., Biochem. Behav.*, 23(5), pp. 831–836 (1985).

M. E. A. Reith et al., "Structural Requirements for Cocaine Congeners to Interact with Dopamine and Serotonin Uptake Sites in Mouse Brain and to Induce Stereotyped Behavior", *Biochem. Parmacol.*, 35(7), pp. 1123–1129.

M. E. A. Reith et al., "Structural Requirements for Cocaine Congeners to Interact with [³H] Bactachotoxinin a 20–α–Benzoate Binding Sites on Sodium Channels in Mouse Brain Synaptosomes", *J. Biol. Chem.*, 261(16), pp. 7300–7305 (1986).

S. M. Roberts et al., "An Assay for Cocaethylene and Other Cocaine Metabolites in Liver Using High–Performance Liquid Chromatography", *Anal. Biochem.*, 202(2), pp. 256–261 (1992).

S. M. Roberts et al., "Cocaethylene Hepatoxicity in Mice", *Biochem. Pharmacol.*, 43(9), pp. 1989–1995 (1992).

R. H. Rohrbaugh and P. C. Jurs, "Prediction of Gas Chromatographic Retenti9on Indexes for Diverse Drug Compounds", *Anal. Chem.*, 60(20), pp. 2249–2253 (1988).

Schmidt and Werner, "Synthetischer Einbau von $^{14}$C in (–)–Cocain, (–)–Edgonin und Derivate", *Ann.*, pp. 184–194 (1962) (Schmidt).

R. M. Smith, "Ethyl Esters of Arylhydroxy–and Arylhydroxymethoxycocaines in the Urines of Simultaneous Cocaine and Ethanol Users", *J. Anal. Toxicol.*, 8(1), pp. 38–42 (1984).

D. L. Von Minden and N. A. D'Amato, "Simultaneous Determination of Cocaine and Benzoylecgonine in Urine by Gas–liquid Chromatography", *Anal. Chem.*, 49(13), pp. 1974–1977 (1977).

G. Werner and K. H. Stoerr, "Labeled Tropane Alkaloids. VI. Synthesis of Psicaine–nue N–Methyl–T1 and of Polytopically Tritiated Psicaine", *Justus Liebigs Ann. Chem.*, (10), pp. 1650–1654 (1974) (Werner).

J. J. Woodward et al., "Cocaethylene Inhibits Dopamine Uptake and Produces Cocaine–Like Actions in Drug Discrimination Studies", *Eur. J. Pharmacol.*, 197(2–3), pp. 235–236 (1991).

I. Zimanyi et al., "Effect of Cocaine and Cocaine Congeners on Veratridine–Induced Depolarization in Mouse Cerebrocortical Synaptoneurosomes", *J. Neurosci. Res.*, 22(2), pp. 201–208 (1989).

DERIVATIVES OF BENZOYLECGONINE, ECGONINE AND ECGONIDINE AND METHODS FOR PREPARING AND USING SAME

CROSS-REFERENCE TO RELATED APPLICATION

This application is a divisional of application Ser. No. 07/999,307, filed Dec. 31, 1992, U.S. Pat. No. 5,376,667.

TECHNICAL FIELD OF THE INVENTION

The present invention relates to a novel class of benzoylecgonine, ecgonine and ecgonidine derivatives which are useful for preventing and treating immunoregulatory disorders, neuromuscular disorders, joint disorders, connective tissue disorders, circulatory disorders and pain. The compounds of this invention are conveniently obtained by chemical synthesis. Accordingly, this invention also relates to methods for preparing the benzoylecgonine, ecgonine and ecgonidine derivatives and to pharmaceutical compositions containing these derivatives.

BACKGROUND OF THE INVENTION

Benzoylecgonine, ecgonine and ecgonidine are known metabolites of cocaine (see, for example, S. M. Roberts et al., "An Assay for Cocaethylene and Other Cocaine Metabolites in Liver Using High-Performance Liquid Chromatography" *Anal Biochem.*, 202, pp 256–61 (1992); D. T. Chia and J. A. Gere, "Rapid Drug Screening Using Toxi-Lab Extraction Followed by Capillary Gas Chromatography/Mass Spectroscopy", *Clin. Biochem.*, 20, pp. 303–06 (1987)). Routes for their preparation have been established (see, for example, A. H. Lewin et al., "2β-Substituted Analogues of Cocaine. Synthesis and Binding to the Cocaine Receptor", *J. Med. Chem.*, 35, pp. 135–40 (1992); M. R. Bell. and S. Archer, "L(+)-2-Tropinone", *J Amer. Chem. Soc.*, 82, pp. 4642–44 (1960)).

We have demonstrated the pharmaceutical efficacy of benzoylecgonine and ecgonine in the treatment of rheumatoid arthritis and osteoarthritis (see, for example, U.S. Pat. Nos. 4,469,700, 4,512,996 and 4,556,663). Unfortunately, the original promise of these compounds has not been fully realized. Due to their low rate of absorption into the blood stream and their low solubility in solution, the effective dose must be relatively high and certain modes of administration (such as topical administration) are less practical. In addition, neither benzoylecgonine nor ecgonine cross the blood/brain barrier. Therefore, these compounds are not effective in treating disorders of the central nervous system.

All the above-mentioned restrictions limit the number of potential uses for benzoylecgonine, ecgonine and ecgonidine. Therefore, a need exists for easily synthesized, stable derivatives of these compounds which will be more easily absorbed into the bloodstream without adverse side effects, while maintaining a high level of therapeutic efficacy.

SUMMARY OF THE INVENTION

It is a principal object of this invention to provide easily synthesized, stable benzoylecgonine, ecgonine and ecgonidine derivatives which overcome the above-mentioned problems and are useful for preventing and treating immunoregulatory disorders, neuromuscular disorders, joint disorders, connective tissue disorders, circulatory disorders and pain.

The benzoylecgonine, ecgonine and ecgonidine derivatives of this invention are represented by the formulas I, II and III, respectively:

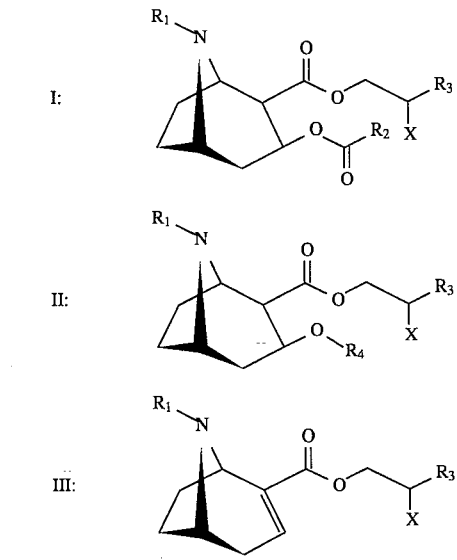

wherein:

$R_1$ is selected from the group consisting of H; branched or unbranched alkyl, alkenyl and alkynyl, optionally substituted by OH, SH, $NH_2$ or halogen; $COCH_3$; COPh; and COBn;

$R_2$ is selected from the group consisting of branched or unbranched alkyl, alkenyl and alkynyl, optionally substituted by OH, SH, $NH_2$ or halogen; aryl; and benzyl;

$R_3$ is selected from the group consisting of branched or unbranched alkyl, alkenyl and alkynyl, optionally substituted by OH, SH, $NH_2$ or halogen;

$R_4$ is selected from the group consisting of H; and branched or unbranched alkyl, alkenyl and alkynyl, optionally substituted by OH, SH, $NH_2$ or halogen; and X is selected from the group consisting of OH; SH; $NH_2$; and halogen.

It is also an object of this invention to provide convenient synthetic methods for preparing the compounds of formulas I, II and III.

It is a further object of this invention to provide pharmaceutical compositions comprising compounds of formulas I, II and III, and mixtures thereof.

It is yet a further object of this invention to provide methods for preventing and treating immunoregulatory disorders, neuromuscular disorders, joint disorders, connective tissue disorders, circulatory disorders and pain using the compounds and pharmaceutical compositions described herein.

DETAILED DESCRIPTION OF THE INVENTION

In accordance with this invention, the following definitions apply:

The following abbreviations are used herein: Bn=benzyl; and Ph=phenyl.

The term "aryl" refers to an aromatic hydrocarbon having from four to seven carbon atoms within the ring, and may be substituted by branched or unbranched alkyl groups having from one to six carbons. Preferably, the ring has six carbon members. Examples of such compounds are tolyl, xylyl, cymyl, mesityl and phenyl. The most preferred aryl is phenyl.

The terms "benzoylecgonine" "ecgonine" and "ecgonidine" refer not only to those compounds, but also to the 2-β acids of the compounds of formulas I, II and III (i.e., their hydrolysis products). For example, the 2-β acid of a compound of formula I will be referred to herein as a benzoylecgonine compound.

The term "branched or unbranched alkyl" refers to a straight chain or branched chain hydrocarbon having one to six carbon atoms. Examples of such alkyl groups are methyl, ethyl, propyl, isopropyl, butyl, isobutyl, pentyl, neopentyl, hexyl and isohexyl.

The terms "branched or unbranched alkenyl" and "branched or unbranched alkynyl" refer to a straight chain or branched chain alkenyl or alkynyl group having from two to six carbon atoms. The alkenyl radicals can be in the cis, trans, E- or Z- form. Examples of such alkenyl groups are vinyl and the radicals of ethylene, propylene, isobutylene, 2-butene and 2-pentene. Examples of alkynyl groups are the radicals of acetylene, propyne, 3-methyl-1-butyne, 4-propyl-2-heptyne and 3-hexyne.

The term "pharmaceutically effective amount" refers to an amount effective in preventing or treating immunoregulatory disorders, neuromuscular disorders, joint disorders, connective tissue disorders, circulatory disorders and pain in a mammal, including a human.

The term "pharmaceutically acceptable carrier or adjuvant" refers to a carrier or adjuvant that may be administered to a mammal, including a human, together with a compound, mixture, or composition of this invention which is non-toxic and does not destroy the pharmacological activity of the compound, mixture or composition of this invention.

The benzoylecgonine, ecgonine and ecgonidine derivatives of this invention are represented by the formulas I, II and III, respectively:

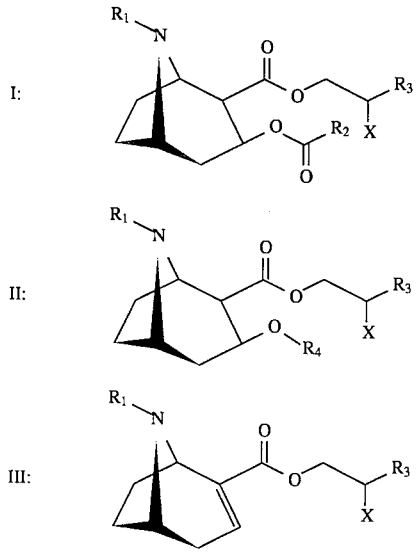

wherein:

$R_1$ is selected from the group consisting of H; branched or unbranched alkyl, alkenyl and alkynyl, optionally substituted by OH, SH, $NH_2$ or halogen; $COCH_3$; COPh; and COBn;

$R_2$ is selected from the group consisting of branched or unbranched alkyl, alkenyl and alkynyl, optionally substituted by OH, SH, $NH_2$ or halogen; aryl; and benzyl;

$R_3$ is selected from the group consisting of branched or unbranched alkyl, alkenyl and alkynyl, optionally substituted by OH, SH, $NH_2$ or halogen;

$R_4$ is selected from the group consisting of H; and branched or unbranched alkyl, alkenyl and alkynyl, optionally substituted by OH, SH, $NH_2$ or halogen; and X is selected from the group consisting of OH; SH; $NH_2$; and halogen.

Preferred compounds of formulas I, II and III are those wherein $R_1$ is selected from the group consisting of H and branched or unbranched alkyl having up to 4 carbon atoms and optionally substituted by OH, SH, $NH_2$ or halogen; $R_2$ is selected from the group consisting of branched or unbranched alkyl optionally substituted by OH, SH, $NH_2$ or halogen; and phenyl; $R_3$ is selected from the group consisting of branched or unbranched alkyl having up to 4 carbon atoms and optionally substituted by OH, SH, $NH_2$ or halogen; $R_4$ is selected from the group consisting of H; and branched or unbranched alkyl having up to 4 carbon atoms and optionally substituted by OH, SH, $NH_2$ or halogen; and X is selected from the group consisting of OH; SH; $NH_2$ and halogen.

More preferred compounds of formulas I, II and III are those wherein $R_1$ is selected from the group consisting of H and $CH_3$; $R_2$ is selected from the group consisting of $CH_3$ and phenyl; $R_3$ is selected from the group consisting of $CH_3$, ethyl, and isopropyl; $R_4$ is selected from the group consisting of H and $CH_3$; and X is selected from the group consisting of OH and $NH_2$.

The most preferred compounds of formulas I, II and III are 2-hydroxypropyl benzoylecgonine (compound IV), 2-hydroxypropyl ecgonine (compound V) and 2-hydroxypropyl ecgonidine (compound VI), respectively:

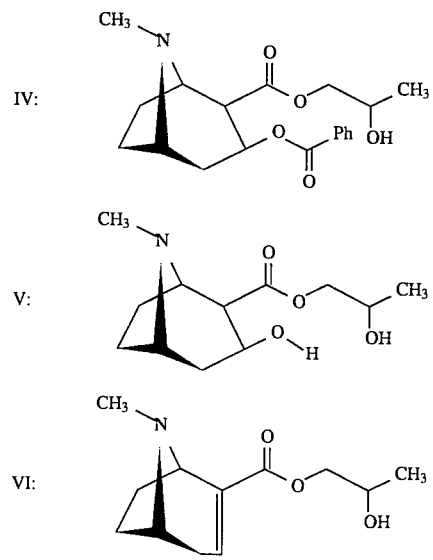

The compounds of formulas I, II and III (including the preferred compounds of formulas IV, V and VI) are useful for preventing and treating immunoregulatory disorders, neuromuscular disorders, joint disorders, connective tissue disorders, circulatory disorders and pain. While not wishing to be bound by theory, we believe that these compounds may act as prodrugs. We believe that under physiological conditions, hydrolysis of the 2-β ester group of these compounds slowly occurs, resulting in the formation of the corresponding benzoylecgonine, ecgonine and ecgonidine compounds, respectively. However, the compounds of this invention may also exhibit efficacy in their original, unhydrolyzed form.

Compounds of formulas I, II and III are more readily absorbed into the bloodstream than the corresponding benzoylecgonine, ecgonine and ecgonidine compounds because of their increased lipophilicity. We believe that the 2-β-(2-X derivatized optionally substituted alkyl) moiety increases the lipophilicity of the compounds of this invention, while maintaining or enhancing the desired properties of the corresponding benzoylecgonine, ecgonine and ecgonidine compounds (such as, for example, chelating ability). By administering the compounds of this invention to a patient, greater amounts of the active ingredient will enter the bloodstream and reach the targeted area than if the benzoylecgonine, ecgonine and ecgonidine compounds themselves were administered at the same dosage level. Accordingly, the pharmaceutical effects of the benzoylecgonine, ecgonine and ecgonidine compounds will be enhanced at a lower dosage level without additional side effects.

Furthermore, pharmacological effects which were previously unattainable using particular modes of administration (such as topical administration) can now be realized, due to the decrease in the required dosage level. And because of their increased solubility in solution, the actual administered amount of a pharmaceutical composition containing the compounds of this invention will be decreased, making the composition more easily applied and the treatment regimen more acceptable to the patient. Consequently, it is possible to effectively administer the compounds of this invention in a wide variety of dosage forms.

In addition, the compounds of formulas I, II and III are able to enter the central nervous system ("CNS") in an amount effective to treat certain CNS disorders (such as, for example, Parkinson's disease), without causing adverse side effects commonly associated with conventional centrally-active drugs (e.g., euphoria, tachycardia and vasoconstriction). We believe that in the prodrug form, the 2-β ester can penetrate the blood/brain barrier but is then hydrolyzed to the corresponding 2-β acid (which could not have passed through the blood/brain barrier). In this manner, pharmaceutically effective amounts of benzoylecgonine, ecgonine and ecgonidine compounds can be successfully targeted at the CNS.

We believe that the compounds of formulas I, II and III in their native, unhydrolyzed form may also be useful in preventing and treating the aforementioned disorders. As the 2-β esters, those compounds may, for example, act peripherally to improve circulation to the afflicted areas. In addition, by increasing the levels of peripherally circulating dopamine (for example, by preventing dopamine re-uptake at the synaptosome), the compounds of this invention may create a chemical sympathectomy.

Although the precise mode of action of the compounds of this invention is not known, one theory is that the compounds of formulas I, II and III undergo a chelation reaction with the fibers of the muscles and joint capsules, allowing the fibers of the connective tissue to relax and become elongated. This elongation of the connective tissue fibers would result in decreased inflammation by increasing circulation and muscle activity and by improving joint motion. This theory explains the positive therapeutic results experienced by patients having joint, neuromuscular, connective tissue and circulatory disorders.

Alternatively, the compounds of formulas I, II and III may act as chelating agents of certain neurotransmitters or co-factors in the body (such as, for example, calcium, sodium and potassium ions). The blood level of free neurotransmitters and co-factors has a direct effect on the functioning of ionic channels and consequently, on intracellular response to various stimuli (such as, for example, intracellular mediation of catecholamine response through the cAMP system). Therefore, the formation of chelation complexes may play a significant role in the pharmacological activity of the compounds of this invention.

Under these chelation theories, the presence of the hydroxy, thiol, amino or halogen moiety at the 2-ε-carbon is particularly important, as we believe that chelation occurs at that site. We prefer hydroxy at this position. We also prefer polyols, especially 1,2- or 1,3-diols (i.e., compounds of this invention having a second hydroxy at the zeta- or eta-carbon). Under the chelation theory, these polyols (including the preferred diols), with their multiple chelation sites, will be particularly active.

Another alternative theory involves the intracellular degradation of the compounds of this invention, resulting in the production of certain analgesic, anti-oxidant and anti-inflammatory compounds (such as benzoic acid and salicylic acid). The in vivo production of such pharmaceutically active compounds would procure the benefit of those agents while avoiding many of the side effects associated with their administration (such as gastrointestinal and renal toxicity). The in vivo production of anti-oxidants might explain the impressive immunoregulatory effects shown by the compounds of this invention. Likewise, the production of analgesics and anti-inflammatory agents in the body would also help to explain the mode of action of the compounds of this invention in preventing and treating pain.

Another possible mode of action involves a reduction in prostaglandin synthesis by inhibiting the action of phospholipase. During conditions of inflammation, pain, fever and platelet aggregation, arachidonic acid is liberated from phospholipid fractions of cell membranes by phospholipase $A_2$. The arachidonic acid is then converted to other products, such as intermediate cyclic endoperoxide prostaglandins. These intermediates produce pain, inflammation and vasoconstriction. Prostaglandins have many other biological actions, including the ability to produce erythema, edema, pain, fever, vasodilation and uterine contractions. Therefore, by inhibiting the synthesis of prostaglandins, many desired physical effects can be realized.

Other possible modes of action include inhibition of chemotaxis of cells implicated in the inflammatory process, inhibition of lysosomal membrane labilization, antagonistic effects on mediators other than prostaglandins (e.g., histamines and bradykinin), inhibition of the biosynthesis of mucopolysaccharides, uncoupling of oxidative phosphorylation, fibrinolytic activity and sulfhydryl-disulfide stabilization. "We have developed" a simple and convenient synthetic route which produces a mixture of benzoylecgonine, ecgonine, ecgonidine, and their 2-hydroxypropyl derivatives (for simplicity, we will refer to this mixture as "the derivative mixture"). In that synthetic route, base cocaine is dissolved in propylene glycol (about 5% base cocaine to about 90% propylene glycol, w/w) then about 5% water (w/w) is added. We then heat the solution at 25° C.–100° C. until substantially all the cocaine has reacted and no additional product forms (typically, about an hour at 100° C. or about 12 days at 50° C.). The reaction time can range from one hour to three weeks depending on the exact reaction conditions used. We prefer to conduct the reaction at 50° C. for about 12 days.

When the reaction is complete, the propylene glycol and water may optionally be removed using conventional means (such as vacuum distillation). The decision to remove the propylene glycol and water will depend on the route of administration to be employed. For example, when the product mixture is to be applied topically, typically the propylene glycol and water will not be removed. However, for other administrative routes (such as oral or intravenous administration), the propylene glycol and water should be removed. We prefer not to remove the solvents and to apply the product mixture as a topical solution in propylene glycol directly to skin or, alternatively, in a transdermal patch.

We have also developed a simple synthetic route for preparing a mixture of 2-hydroxypropyl ecgonine and 2-hydroxypropyl ecgonidine. In that reaction scheme, ecgonine is dissolved in propylene glycol and the solution is heated at about 25° C.–115° C. until substantially all the ecgonine has reacted and no additional product forms (typically, about 7 days at 100° C.). The propylene glycol is then removed using conventional means (such as vacuum distillation). If desired, the individual compounds may be easily separated and purified from the mixture using conventional techniques (such as fractional collection chromatography or fractional recrystallization).

We have also developed a simple synthetic route for preparing 2-hydroxypropyl benzoylecgonine. In that synthetic scheme, cocaine base is dissolved in propylene glycol. No water is added. The solution is then heated at about 25° C.–115° C. until substantially all the cocaine has reacted and no additional product forms (typically, about 4 days at 100° C.). The propylene glycol is then removed using conventional means (such as vacuum distillation). The product can then be purified using conventional techniques (such as recrystallization).

As can be appreciated by a chemist of ordinary skill in the art, the simple synthetic schemes described above can be modified to produce any of the compounds of formulas I, II and III. Such modifications might involve alterations in the starting materials (such as the use of glycols other than propylene glycol or the use of an alcohol in an inert solvent in a transesterification reaction) or the addition of further synthetic steps (such as functional group transformations). Depending on precisely how the synthetic scheme is modified, the specific reaction conditions (such as the precise temperature and reaction times) might also require modification. Since the progress of the reaction can be easily monitored by techniques such as high performance liquid chromatography, gas chromatography, mass spectroscopy thin layer chromatography, nuclear magnetic resonance spectroscopy and the like, such modifications are well within the skill of the art.

The compounds of this invention, and mixtures thereof, may be administered alone or in combination with other compounds, such as, for example, benzoylecgonine, ecgonine or ecgonidine compounds. When a combination of the compounds of formula I, II or III are administered together with benzoylecgonine, ecgonine or ecgonidine, the therapeutic efficacy of the latter compounds is enhanced. We prefer that pharmaceutical compositions comprising a combination of the compounds of this invention with benzoylecgonine, ecgonine and ecgonidine contain at least 5%, but more preferably at least 10%, of the compounds of formulas I, II and III (w/w).

This invention also envisions the administration of the compounds of formula I, II and III in combination with conventional therapeutic agents. Advantageously, such combination therapies utilize lower dosages of those conventional therapeutics, thus avoiding possible toxicity and adverse side effects incurred when those agents are used as monotherapies. For example, the compounds of this invention may be used in combination with conventional cancer drugs (such as, for example, methotrexate, taxol, 5-fluorouracil, cis-platinum, cortisone, nitrogen mustards, thiotepa and nitrosoureas), arthritis drugs (such as, for example, non-steroidal anti-inflammatory agents, penicillamine, methotrexate, cortisone and gold salts) and neurological agents (such as, for example, amantadine, L-DOPA and CNS-anticholinergics).

According to this invention, the compounds of formulas I, II and III, and the pharmaceutical compositions containing those compounds, or mixtures thereof, may be administered to any mammal, including a human. The compounds and pharmaceutical compositions of this invention may be administered in any pharmaceutically acceptable dosage form, including, but not limited to intravenously, intramuscularly, subcutaneously, intra-articularly, intrasynovially, intrathecally, periostally, intratumorally, peritumorally, intralesionally, perilesionally, by infusion, sublingually, buccally, transdermally, orally, topically or by inhalation. We prefer topical administration or administration by inhalation.

Dosage forms may include pharmaceutically acceptable carriers and adjuvants which are known to those of skill in the art. These carriers and adjuvants include, for example, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Adjuvants for topical or gel base forms of the compounds and compositions of this invention include, but are not limited to, sodium carboxymethylcellulose, polyacrylates, waxes, polyoxyethylene-polyoxypropylene-block polymers, polyethylene glycol, propylene glycol and wool fat.

For all administrations, conventionally administered dosage forms may be used. Such forms include, for example, tablet, capsule, caplet, liquid, solution, suspension, emulsion, lozenges, syrup, reconstitutable powder, granule, suppository and transdermal patch. Methods of preparing such dosage forms are known (see, for example, H. C. Ansel and N. G. Popovish, *Pharmaceutical Dosage Forms and Drug Delivery Systems,* 5th edition, Lea and Febiger 1990).

The compounds and pharmaceutical compositions of this invention may be employed in a conventional manner for the prevention or treatment of any of the aforementioned disorders. Such methods of prophylaxis and treatment and their dosage levels and requirements are well-recognized in the art and may be chosen by those of ordinary skill in the art from the available methods and techniques. Typically, dosage levels range from about 25–200 mg/dose for a 70 kg patient. Although one dose per day is often sufficient, up to 5 doses/day may be given. For oral doses, up to 1500 mg/day may be required. A typical treatment regimen for a 70 kg patient with a joint disorder (such as rheumatoid arthritis) or an immunoregulatory disorder (such as an autoimmune disease) is four doses/day (200 mg/dose) topically applied for two weeks. However, some disorders (such as osteoarthritis) require only 1 dose/day for two days. Once the symptoms of the disorder have receded, maintenance doses can be administered on a p.r.n. basis. As the skilled artisan will appreciate, lower or higher doses than those recited above may be required. Specific dosage and treatment regimens will depend on such factors as the patient's general health status, the severity and course of the patient's disorder or disposition thereto and the judgment of the treating physician.

Immunoregulatory disorders that may be prevented or treated with the compounds and compositions of this invention include, but are not limited to: inflammation, autoimmune diseases, allergies (such as, for example, insect bites and stings (e.g., mosquito, fire ant, bee or fly), poison ivy, poison oak and contact dermatitis.

Neuromuscular disorders that may be prevented or treated with the compounds and compositions of this invention include, but are not limited to: amyotrophic lateral sclerosis, multiple sclerosis, skeletal muscle trauma, spasm post-stroke, loss of sensory acuity, weakness, cerebral edema, Reiter's syndrome, polymyositis, Parkinson's disease, Huntington's disease, angina and acute back strain.

Joint disorders that may be prevented or treated with the compounds and compositions of this invention include, but are not limited to: restricted range of motion, post-fracture contracture, arthritis (such as, for example, rheumatoid arthritis, osteoarthritis, mixed arthritis, psoriatic arthritis, gout, inflammatory gout or juvenile rheumatoid arthritis), bursitis, ankylosing spondylitis, rheumatoid vasculitis and joint rigidity.

Connective tissue disorders that may be prevented or treated with the compounds and compositions of this invention include, but are not limited to: systemic lupus, Burger's disease, periarteritis nodosum, proliferative diseases (e.g., keloid scar formation, excessive scar formations, sanctity of scarified fibers and proliferative cancers such as carcinomas and sarcomas), scleroderma and collagen disorders.

Circulatory disorders that may be prevented or treated with the compounds and compositions of this invention include, but are not limited to: angina pectoris, myocardial ischemia, gangrene and diabetes (such as diabetes mellitus and diabetes insipidus).

In order that this invention be more fully understood, the following examples are set forth. These examples are for the purpose of illustration only, and are not to be construed as limiting the scope of the invention in any way.

CHEMICAL SYNTHESES

In the following examples, these instruments and procedures were used:

GC/MS analyses were performed on a Finnigan Model 9610 gas chromatograph-4000 Mass Spectrometer equipped with an IBM-AT computer using Teknivent Vector/one data system software (St. Louis, Mo.). The mass spectrometer was calibrated using perfluorotributylamine. Chromatographic separations were achieved on a 30 mm × 0.32 mm, 0.25 μm film thickness (BD-1, J&W Scientific, Folson, Calif.) dimethysilicone fused silica capillary column. Ultra pure helium was used as the carrier gas and compressed air was used as the make up gas (Sunox Inc., Charleston, S.C.).

Reagents and samples were weighed on a microbalance type 2406 (range 0–20 g, Sartorius Werke GMBH Gottigen, Germany), microbalance type 4503 (range 0–1 g, Sartorius Werke GMBH (Gottingen, Germany), or a microbalance type 2842 (range 0–160 g, Sartorius Werke GMBH Gottigen, Germany).

A Vortex-Genie (Scientific Industries, Inc. Bohemia, N.Y.) was used to mix standards.

A Varian Aerograph series 1400 gas chromatographic oven was used to heat all samples requiring derivatization.

A Fisher Isotem 500 series drying oven was used for drying glassware.

Three necked round bottomed flasks (250 ml, 50 ml, 100 ml and 500 ml) were used for synthesis. Centrifuge tubes (15 ml) were silanized with a solution of dimethyldichlorosilane in toluene. Disposable borosilicate pipettes (1, 5, and 10 ml) by Fisher Scientific Company were used. Derivatizing reactions were carried out using teflon lined 1, 2, and 3 dram vials. All other glassware was routine scientific glassware for synthetic or analytical purposes.

The HPLC analyses were performed with an HPLC system which consisted of a Beckman M-45 delivery pump, Model Lambda Max 481 LC spectrophotometer variable wavelength UV absorbance detector equipped with an automatic sampling Wisp injector model 710B, accessory and a Shimadzu C-R3A Chromatopac integrator. The stationary phase was a reversed phase $C_{18}$ column (μm Bondapak of Millipore, P/N 27324, (3.9 mm ID × 30 cm.)

All HPLC analyses were performed with the UV detector operating at 232 wavelength. The mobile phase was 20% v/v acetonitrile in 0.01 M $KHPO_4$ (pH range 2.1–2.9) with a flow rate of 2.0 ml/min. The injection volume was 15 μl and operating range as 0.1 AUFS. No internal standard was utilized for the HPLC assay.

A filter holder (Fisher brand) assembly with a 300 ml fritglass support (47 mm) was used to degas the HPLC mobile phase.

Filter papers (0.22μ, Lazar Scientific, Los Angeles, Calif.) were used to filter the mobile phase for the HPLC assay.

Homatropine hydrobromide, pentafluoropropionic anhydride (PFPA), and pentafluoropropanol (PFP) were obtained from Aldrich Chemical Co. (Milwaukee, Wis.).

A high line vacuum was used to evaporate or distill propylene glycol solution.

Solvents from derivatization were removed by evaporating (with evaporating needles) under a stream of nitrogen. Solvents requiring heat during evaporation were heated in a sand bath.

All mass spectrometric analyses utilized the Finnigan system. The helium gas linear velocity was at 50 cm/s. The data system scan rate was every 0.2 s with a sweep width of 0.1μ, integrating each acquisition sample for 4 ms. Perfluorotributylamine was used to calibrate the MS. Electron impact ionizing voltage was at 60 eV and ionizing current at 300 μA. The electron multiplier was operated at 1700 V. With injection port and MX ion source temperature set at 250° C. and 260° C. respectively, separation was achieved using a multi-linear programmed temperature initially at 130° C. and increased to 140° C. at 2°/min, then finally to 258° C. at 17°/min. When isothermal conditions were used, the column temperature was maintained at 160° C., 185° C., 200° C., or 220° C. For a typical analytical procedure, 0.05 μl or 0.1 μl with an equal amount of air was quickly injected into the GC injection port. Upon injection of the sample, temperature programming was begun, acquisition monitored, and the filament activated 1.5 min after injection of sample.

Derivatization of the compounds was performed before GC/MS analysis. 10 μl of the compound to be derivatized was placed in a teflon capped vial and derivatized with the 35 μl volume of PFP and 70 μl PFPA. The vial was heated at 100° C. for 20 min, cooled, excess reagents evaporated, reconstituted with acetonitrile to the desired volume, and then analyzed on GC/MS.

Cocaine base was prepared by the following protocol: Cocaine HCl (5.0 g) was dissolved in 150 ml of distilled water. Volumes of 1 N KOH were added with stirring to a final pH of about 10. The white solid formed was padded dry using filter paper and paper towel. The solid was then placed in a 500 ml beaker and allowed to melt in a 100° C. to 110° C. oil bath. Once the solid was completely melted, the beaker was removed and allowed to cool to room temperature. The excess water was decanted and the crystallized cocaine base was allowed to air dry.

Benzoylecgonine was synthesized by the following protocol: Cocaine base (9.3 g) was mixed with 200 ml of distilled water and allowed to reflux for 5 hr. The resultant solution was cooled and extracted five times with diethyl ether. The aqueous layer was evaporated under reduced pressure and the residue was recrystallized from water. Needle shaped white crystals were collected (approximate yield: 50%).

Ecgonine HCl was synthesized by direct acid hydrolysis of cocaine using the protocol described in M. R Bell and S. Archer, "L(+)-2-Tropinone" *J. Amer. Chem. Soc.*, 82, pp. 4642–44 (1960): Cocaine HCl (9.0 g) was dissolved in 10 ml of 12 N HCl and 150 ml of distilled water and refluxed for 15 hr. The resultant solution was cooled and extracted five times with diethyl ether, the aqueous phase was combined and evaporated under reduced pressure. The residue was recrystallized from ethanol and water to yield white crystals (approximate yield: 50%).

Structure elucidation was performed by GC/MS and confirmed by the observed retention times of the fluorinated derivatives and the observed MS fingerprint fragment ions.

EXAMPLE 1

Synthesis of 2-Hydroxypropyl Benzoylecgonine 500 mg of cocaine base was placed in a round bottomed flask, to which 20 ml of propylene glycol was added. The solution was stirred until all the cocaine had dissolved. Then the temperature was gradually increased to about 100° C. and the solution was allowed to stir for approximately 4 days. The reaction was monitored periodically by GC/MS. Once the cocaine peak substantially disappeared from the GC trace, the reaction mixture was allowed to cool to room temperature. Excess propylene glycol was removed by vacuum distillation (5 mm Hg). Fractional recrystallization (using an ethanol/ether system) yielded the product 2-hydroxypropyl benzoylecgonine. GC/MS: m/z =347; retention time =9.55 min.

EXAMPLE 2

Synthesis of 2-Hydroxypropyl Ecgonine and 2-Hydroxypropyl Ecgonidine 500 mg of ecgonine HCl was placed in a round bottomed flask. 20 ml of propylene glycol was added and the solution was stirred until all the ecgonine had dissolved. The temperature was gradually increased to about 100° C. The reaction was monitored by GC/MS. When substantially all the ecgonine had reacted (after approximately 7 days), the solution was cooled to room temperature and the propylene glycol was removed by vacuum distillation at 7.5 mm Hg. The compounds were separated by fractional collection chromatography using an ammonia/ethanol solution as the eluting solvent. GC/MS: 2-hydroxypropyl ecgonine (m/z =243; retention time =5.28 min.); 2-hydroxypropyl ecgonidine (m/z =27; retention time =4.57 min.)

EXAMPLE 3

Synthesis of the Derivative Mixture (5% Solution in Propylene Glycol)

270.0 g of propylene glycol and 15.0 g of distilled water were placed in a 500 ml round bottomed flask fitted with a thermometer and a magnetic stirring bar. The solution was heated to 50° C. with stirring. 15.0 g of cocaine base was added to the warmed solution. The solution was allowed to stir for twelve days, after which less than 0.1% of the cocaine base remained.

GC/MS revealed the following composition of the active compounds (comprising 5% of the total weight of the composition):

Benzoylecgonine =65%
Ecgonine =10%
Ecgonidine =2%
2-hydroxypropyl Benzoylecgonine =5%
2-hydroxypropyl Ecgonine =12%
2-hydroxypropyl Ecgonidine =6%

PATIENT TREATMENTS

In all of the patient treatment examples which follow, the derivative mixture was administered topically to the afflicted areas. Each dose comprised 200 mg of the derivative mixture, applied as a 5% solution in propylene glycol as prepared in Example 3 (approx. 4 cc), unless otherwise specified.

EXAMPLE 4

The following four patients suffering from rheumatoid arthritis were treated with 1–3 doses/day of the derivative mixture (applied to the arms and legs):

Patient 1 (male, 34 years old, 75 kg (170 lbs.))
Patient 2 (male, 35 years old, 75 kg (170 lbs.))
Patient 3 (female, 40 years old, 55 kg (120 lbs.))
Patient 4 (female, 60 years old, 45 kg (100 lbs.))

After two weeks of treatment, each of the patients experienced a marked improvement in range of motion of the afflicted joints, reduction of swelling and pain and an increase in strength.

Patient 1 received a maintenance dose of the derivative mixture once a day for an additional 2 weeks. After stopping the treatment, the symptoms of the disease returned within 2 days.

Patient 2 received a maintenance dose of the derivative mixture once a day for 4 weeks. His symptoms did not return after 6 months.

Patient 3 received a maintenance dose of the derivative mixture once a day for 3 months. The symptoms of the disease did not return after 6 months.

Patient 4 did not receive any maintenance treatment. Her symptoms returned after 2 days of stopping the treatment.

EXAMPLE 5

One male patient with ankylosing spondylitis, 25 years old and weighing 75 kg (170 lbs.), was treated with 2 doses/day of the derivative mixture. Prior to treatment, the patient's symptoms included severe pain, restricted range of motion and difficulty breathing. After 2 weeks of treatment, the patient's symptoms had completely disappeared. The patient did not receive any maintenance treatment. The symptoms did not return after 2 months.

EXAMPLE 6

One male patient with Parkinson's disease and rheumatoid arthritis (70 years old, 60 kg (130 lbs.)) and one female patient with Parkinson's disease and rheumatoid arthritis (45 years old, 50 kg (110 lbs.)) were treated with 3 doses/day of the derivative mixture. Prior to treatment, their symptoms included severe tremors and pain, inability to speak and joint rigidity. After 2 weeks, the symptoms had significantly receded. The symptoms of the disease returned after 1 day of stopping the treatment.

EXAMPLE 7

Two patients with myocardial ischemia (Patient 1: female, 70 years old, 55 kg (120 lbs.); Patient 2: male, 70 years old, 75 kg (170 lbs.)) were treated with 3 doses/day of the derivative mixture (applied to the chest). Prior to treatment, the patients' symptoms included coughing up blood, pain, difficulty breathing and fatigue. After two weeks of treatment, the patients were no longer coughing and were able to exert themselves with greater ease and less pain.

Patient 1 received a maintenance dose of the derivative mixture once a day for 3 years. The symptoms of the disease did not return during that time.

Patient 2 received a maintenance dose of the derivative mixture in varying amounts (from 1–3 doses/day) for 6 weeks. After discontinuing treatment, the angina returned within 2 weeks.

EXAMPLE 8

40 patients with osteoarthritis (25 male, 15 female; ranging in age from 50–70 years) were treated with 1 dose/day of the derivative mixture for 2 days. Each patient experienced a decrease in pain and an increase in range of motion and function of the extremities. The patients all remained symptom free for approximately 6 weeks after stopping the treatment.

EXAMPLE 9

One male patient with Burger's disease (70 years old, weighing 65 kg (140 lbs.)) was treated with 3 doses/day of the derivative mixture (300 mg/dose as a 5% solution in propylene glycol; approximately 6 cc/dose). Prior to treatment, the patient suffered from severe inflammation and gangrene. After 10 days of treatment, the inflammation was gone and the skin returned to its normal color and texture. The patient continued with a maintenance treatment of 1 dose/day (200–400 mg/dose) for 3 months. The symptoms of the disease did not return after 3 years.

EXAMPLE 10

A 6-month old male with juvenile arthritis was treated with 3 doses/day (0.25–0.50 cc/dose; 50–100 mg of the derivative mixture/dose). The symptoms of the disease were markedly decreased after 5 days. After 3 weeks, the disease was in remission. No maintenance treatment was administered. The patient's symptoms did not return after 4 months.

What is claimed is:

1. A mixture of compounds comprising ecgonine, benzoylecgonine, ecgonidine, 2-hydroxypropyl ecgonine, 2-hydroxypropyl benzoylecgonine and 2-hydroxypropyl ecgonidine.

2. The mixture according to claim 1, wherein the mixture is a solution.

3. The mixture according to claim 2, wherein the solution is a propylene glycol solution.

4. The mixture according to claim 3, wherein less than 0.1% cocaine base is present in the solution.

5. A pharmaceutical composition comprising a mixture of two or more compounds, each compound being independently selected from the group consisting of compounds represented by formula I, formula II and formula III:

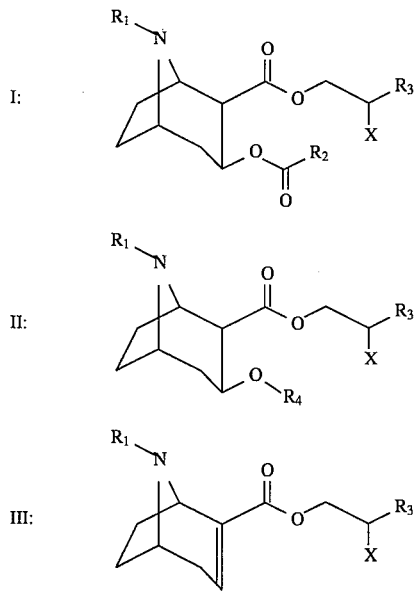

wherein:
  each $R_1$ is independently selected from the group consisting of H; branched or unbranched $C_1$–$C_6$ alkyl, $C_2$–$C_6$ alkenyl and $C_2$–$C_6$ alkynyl, optionally substituted by OH, SH, $NH_2$ or halogen; $COCH_3$; COPh; and COBn;
  each $R_2$ is independently selected from the group consisting of branched or unbranched $C_1$–$C_6$ alkyl, $C_2$–$C_6$ alkenyl and $C_2$–$C_6$ alkynyl, optionally substituted by OH, SH, $NH_2$ or halogen; an aromatic hydrocarbon having from four to seven carbon atoms within the ring, optionally substituted by branched or unbranched $C_1$–$C_6$ alkyl; and benzyl;
  each $R_3$ is independently selected from the group consisting of branched or unbranched $C_1$–$C_6$ alkyl, $C_2$–$C_6$ alkenyl and $C2$-$C_6$ alkynyl, optionally substituted by OH, SH, $NH_2$ or halogen;
  each $R_4$ is independently selected from the group consisting of H; and branched or unbranched $C_1$–$C_6$ alkyl, $C_2$–$C_6$ alkenyl and $C_2$–$C_6$ alkynyl, optionally substituted by OH, SH, $NH_2$ or halogen; and
  each X is independently selected from the group consisting of OH; SH; $NH_2$ and halogen;
and a pharmaceutically acceptable adjuvant or carrier.

6. The pharmaceutical composition according to claim 5, wherein said composition comprises 2-hydroxypropyl ecgonine, 2-hydroxypropyl benzoylecgonine and 2-hydroxypropyl ecgonidine.

7. A pharmaceutical composition comprising:
  (1) a mixture of two or more compounds, each compound being independently selected from the group consisting of compounds represented by formula I, formula II and formula III:

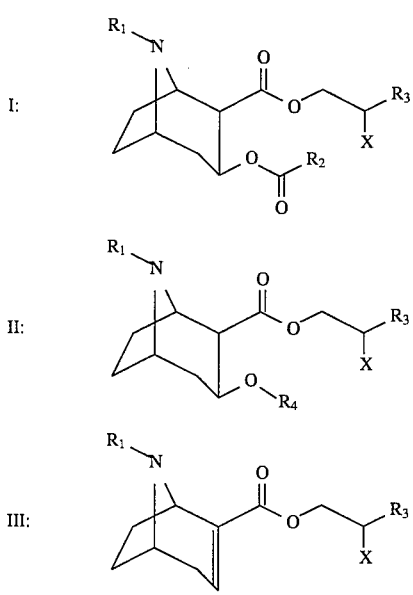

wherein:

each $R_1$ is independently selected from the group consisting of H; branched or unbranched $C_1$–$C_6$ alkyl, $C_2$–$C_6$ alkenyl and $C_2$–$C_6$ alkynyl, optionally substituted by OH, SH, $NH_2$ or halogen; $COCH_3$; COPh; and COBn;

each $R_2$ is independently selected from the group consisting of branched or unbranched $C_1$–$C_6$ alkyl, $C_2$–$C_6$ alkenyl and $C_2$–$C_6$ alkynyl, optionally substituted by OH, SH, $NH_2$ or halogen; an aromatic hydrocarbon having from four to seven carbon atoms within the ring, optionally substituted by branched or unbranched $C_1$–$C_6$ alkyl; and benzyl;

each $R_3$ is independently selected from the group consisting of branched or unbranched $C_1$–$C_6$ alkyl, $C_2$–$C_6$ alkenyl and $C_2$–$C_6$ alkynyl, optionally substituted by OH, SH, $NH_2$ or halogen;

each $R_4$ is independently selected from the group consisting of H; and branched or unbranched $C_1$–$C_6$ alkyl, $C_2$–$C_6$ alkenyl and $C_2$–$C_6$ alkynyl, optionally substituted by OH, SH, $NH_2$ or halogen; and each X is independently selected from the group consisting of OH; SH; $NH_2$ and halogen;

(2) at least one additional compound selected from the group consisting of benzoylecgonine, ecgonine and ecgonidine, and (3) a pharmaceutically acceptable adjuvant or carrier.

8. The pharmaceutical composition according to claim 7, comprising a mixture of compounds consisting of ecgonine, benzoylecgonine, ecgonidine, 2-hydroxypropyl ecgonine, 2-hydroxypropyl benzoylecgonine and 2-hydroxypropyl ecgonidine.

9. The pharmaceutical composition according to claim 5 or 7, wherein said mixture of compounds comprises at least 5% of the total weight of the composition.

10. The pharmaceutical composition according to claim 5 or 7, wherein the pharmaceutically acceptable adjuvant or carrier is propylene glycol.

11. The pharmaceutical composition according to claim 5 or 7, wherein the composition is in an administering dosage form selected from the group consisting of a tablet, capsule, caplet, liquid, solution, suspension, emulsion, lozenges, syrup, reconstitutable powder, granule, suppository and transdermal patch.

12. The pharmaceutical composition according to claim 11, wherein the administering dosage form is a topical solution or transdermal patch.

13. A method for treating a disorder selected from the group consisting of:

(1) inflammation;

(2) a neuromuscular disorder selected from the group consisting of Parkinson's disease, angina and acute back strain;

(3) a joint disorder selected from the group consisting of restricted range of motion, post-fracture contracture, arthritis, bursitis and ankylosing spondylitis;

(4) a connective tissue disorder selected from the group consisting of systemic lupus, Burger's disease and collagen disorders;

(5) myocardial ischemia; and (6) pain;

comprising the step of administering to a mammal a pharmaceutically effective amount of a pharmaceutical composition comprising a compound selected from the group consisting of compounds represented by formula I, formula II and formula III as defined in claim 37 and a pharmaceutically acceptable adjuvant or carrier.

14. The method according to claim 13, wherein the pharmaceutical composition is administered intravenously, intramuscularly, subcutaneously, intra-articularly, intrasynovially, intrathecally, periostally, intratumorally, peritumorally, intralesionally, perilesionally, by infusion, sublingually, bucally, transdermally, orally, topically or by inhalation.

15. The method according to claim 14, wherein the pharmaceutical composition is administered transdermally, topically or by inhalation.

* * * * *

UNITED STATES PATENT AND TRADEMARK OFFICE
CERTIFICATE OF CORRECTION

PATENT NO. : 5,559,123
DATED : September 24, 1996
INVENTOR(S) : Lowell M. Somers, et al.

It is certified that error appears in the above-identified patent and that said Letters Patent is hereby corrected as shown below:

Cover Page, Item [56], Delete first occurrence of "J.R. Fozard et al., "Structure-Activity Relationship of Compounds Which Block Receptors for 5-Hydroxytryptamine on the Sympathetic Nerves of the Rabbit Heart", Br. J. Pharmacol., 61(3), pp. 499P-500P (1977)."

Cover Page, Item [56], in "M.E.A. Reith" (2nd occurrence) -- (1986) -- after "1123-1129".

Cover Page, Item [56], in "R.H. Rohrbaugh", change "Retenti9on" to -- Retention --.

Cover Page, Item [56], in "Schmidt" change "(-)-Edgonin" to -- (-)-Ekgonin --.

Column 16, line 40 change "37" to -- 7 --.

Column 4, line 14 change "group-consist-" to -- group consist- --.

Column 6, line 49 change ""We" to, new paragraph, -- We -- and change "developed"" to -- developed --.

UNITED STATES PATENT AND TRADEMARK OFFICE
CERTIFICATE OF CORRECTION

PATENT NO. : 5,559,123
DATED : September 24, 1996
INVENTOR(S) : Lowell M. Somers, et al.

It is certified that error appears in the above-identified patent and that said Letters Patent is hereby corrected as shown below:

Column 11, line 67 change "27" to -- 227 --.

Column 10, line 23 change "was,used" to -- was used --.

Signed and Sealed this

Nineteenth Day of September, 2000

Attest:

Q. TODD DICKINSON

*Attesting Officer*  *Director of Patents and Trademarks*